US009045753B2

(12) United States Patent
Zhu et al.

(10) Patent No.: US 9,045,753 B2
(45) Date of Patent: Jun. 2, 2015

(54) SIRNA MOLECULE FOR INHIBITING GROWTH OF MELANIN AND APPLICATION THEREOF

(71) Applicant: Jiangsu Genecon Biotechnologies Co., Ltd., Nantong (CN)

(72) Inventors: Yuanyuan Zhu, Jiangsu (CN); Tiejun Li, Jiangsu (CN)

(73) Assignee: Jiangsu Genecon Biotechnologies Co., Ltd., Nantong (CN)

( * ) Notice: Subject to any disclaimer, the term of this patent is extended or adjusted under 35 U.S.C. 154(b) by 0 days.

(21) Appl. No.: 14/354,532

(22) PCT Filed: Oct. 9, 2012

(86) PCT No.: PCT/CN2012/082612
§ 371 (c)(1),
(2) Date: Apr. 25, 2014

(87) PCT Pub. No.: WO2013/060230
PCT Pub. Date: May 2, 2013

(65) Prior Publication Data
US 2014/0336371 A1    Nov. 13, 2014

(30) Foreign Application Priority Data

Oct. 27, 2011    (CN) .......................... 2011 1 0331472

(51) Int. Cl.
| A61K 48/00 | (2006.01) |
| C07H 21/02 | (2006.01) |
| C07H 21/04 | (2006.01) |
| C12N 15/113 | (2010.01) |
| A61K 8/60 | (2006.01) |
| A61Q 19/02 | (2006.01) |

(52) U.S. Cl.
CPC .......... *C12N 15/113* (2013.01); *C12N 2310/14* (2013.01); *A61K 8/606* (2013.01); *A61Q 19/02* (2013.01); *A61K 2800/42* (2013.01)

(58) Field of Classification Search
USPC .................................... 514/44; 536/23.1, 24.5
See application file for complete search history.

(56) References Cited

FOREIGN PATENT DOCUMENTS

| CN | 101601635 A | 12/2009 |
| JP | 2008115101 A | 5/2008 |
| WO | 2013060230 | 5/2013 |

OTHER PUBLICATIONS

Du, J. et al., GenBank Accession No. NM 198178.1, Nov. 4, 2003.
Dou, K. et al., "Suppression of Melanin formation of A375 Cells by Small Interfering RNA", Chinese Journal of Cell Biology, Dec. 31, 2007, vol. 29, No. 4, pp. 617-622, See Abstract.
International Search Report for international application No. PCT/CN2012/082612, filed Sep. 10, 2012, Search report mailed on Jan. 17, 2013.

*Primary Examiner* — Terra Cotta Gibbs
(74) *Attorney, Agent, or Firm* — K&L Gates LLP; Louis C. Cullman; Michelle Glasky Bergman (57) ABSTRACT

Provided is a double-chain siRNA molecule targeting a microphthalmia-associated transcription factor MITF coding gene. A sense strand of the siRNA molecule has a sequence of SEQ ID NO: 3 and an anti-sense strand has a sequence of SEQ ID NO: 4, and the anti-sense strand specifically binds to mRNA of the MITF coding gene, to degrade the mRNA, thereby reducing the synthesis of melanin. Further provided is an application of the siRNA molecule in freckle whitening cosmetics or the preparation of medicines for treatment of diseases related to melanin gene.

3 Claims, 6 Drawing Sheets

SEQUENCE LISTING

```
<160> NUMBER OF SEQ ID NOS: 18

<210> SEQ ID NO 1
<211> LENGTH: 527
<212> TYPE: DNA
<213> ORGANISM: Homo sapiens

<400> SEQUENCE: 1
aggtgcagac ccacctcgaa aaccccacca agtaccacat acagcaagcc caacggcagc      60
aggtaaagca gtacctttct accactttag caaataaaca tgccaaccaa gtcctgagct     120
tgccatgtcc aaaccagcct ggcgatcatg tcatgccacc ggtgccgggg agcagcgcac     180
ccaacagccc catggctatg cttacgctta actccaactg tgaaaaagag ggatttata      240 agtttgaaga gcaaaacagg gcagagagcg agtgcccagg catgaacaca cattcacgag     300
cgtcctgtat gcagatggat gatgtaatcg atgacatcat tagcctagaa tcaagttata     360
atgaggaaat cttgggcttg atggatcctg ctttgcaaat ggcaaatacg ttgcctgtct     420
```

```
cgggaaactt gattgatctt tatggaaacc aaggtctgcc cccaccaggc ctcaccatca    480
gcaactcctg tccagccaac cttcccaaca taaaaaggga gctcaca                 527

<210> SEQ ID NO 2
<211> LENGTH: 683
<212> TYPE: DNA
<213> ORGANISM: Homo sapiens

<400> SEQUENCE: 2
agtctgaagc aagagcactg gccaaagaga ggcagaaaaa ggacaatcac aacctgattg     60
aacgaagaag aagatttaac ataaatgacc gcattaaaga actaggtact ttgattccca    120
agtcaaatga tccagacatg cgctggaaca agggaaccat cttaaaagca tccgtggact    180
atatccgaaa gttgcaacga gaacagcaac gcgcaaaaga acttgaaaac cgacagaaga    240
aactggagca cgccaaccgg catttgttgc tcagaataca ggaacttgaa atgcaggctc    300
gagctcatgg actttccctt attccatcca cgggtctctg ctctccagat ttggtgaatc    360
ggatcatcaa gcaagaaccc gttcttgaga actgcagcca agacctcctt cagcatcatg    420
cagacctaac ctgtacaaca actctcgatc tcacggatgg caccatcacc ttcaacaaca    480
acctcggaac tgggactgag gccaaccaag cctatagtgt ccccacaaaa atgggatcca    540
aactggaaga catcctgatg gacgacaccc tttctcccgt cggtgtcact gatccactcc    600
tttcctcagt gtccccggga gcttccaaaa caagcagccg gaggagcagt atgagcatgg    660
aagagacgga gcacacttgt tag                                            683

<210> SEQ ID NO 3
<211> LENGTH: 25
<212> TYPE: RNA
<213> ORGANISM: Artificial Sequence
<220> FEATURE:
<223> OTHER INFORMATION: siRNA sense strand targeting the MITF gene
<220> FEATURE:
<221> NAME/KEY: misc_feature
<222> LOCATION: (24)..(25)
<223> OTHER INFORMATION: n is a, c, g, or u

<400> SEQUENCE: 3
gggacacuga ggaaaggagu ggann                                           25

<210> SEQ ID NO 4
<211> LENGTH: 25
<212> TYPE: RNA
<213> ORGANISM: Artificial Sequence
<220> FEATURE:
<223> OTHER INFORMATION: siRNA antisense strand targeting the MITF gene
<220> FEATURE:
<221> NAME/KEY: misc_feature
<222> LOCATION: (24)..(25)
<223> OTHER INFORMATION: n is a, c, g, or u

<400> SEQUENCE: 4
uccacuccuu uccucagugu cccnn                                           25

<210> SEQ ID NO 5
<211> LENGTH: 23
<212> TYPE: RNA
<213> ORGANISM: Artificial Sequence
<220> FEATURE:
<223> OTHER INFORMATION: siRNA backbone sense strand targeting the MITF
      gene

<400> SEQUENCE: 5
```
gggacacuga ggaaaggagu gga                                      23

<210> SEQ ID NO 6
<211> LENGTH: 23
<212> TYPE: RNA
<213> ORGANISM: Artificial Sequence
<220> FEATURE:
<223> OTHER INFORMATION: siRNA antisense strand targeting the MITF gene

<400> SEQUENCE: 6
uccacuccuu uccucagugu ccc                                      23

<210> SEQ ID NO 7
<211> LENGTH: 21
<212> TYPE: DNA
<213> ORGANISM: Artificial Sequence
<220> FEATURE:
<223> OTHER INFORMATION: MITF conserved region 1 upstream primer

<400> SEQUENCE: 7
aggtgcagac ccacctcgaa a                                        21

<210> SEQ ID NO 8
<211> LENGTH: 22
<212> TYPE: DNA
<213> ORGANISM: Artificial Sequence
<220> FEATURE:
<223> OTHER INFORMATION: MITF conserved region 1 downstream primer

<400> SEQUENCE: 8
tgtgagctcc ctttttatgt tg                                       22

<210> SEQ ID NO 9
<211> LENGTH: 21
<212> TYPE: DNA
<213> ORGANISM: Artificial Sequence
<220> FEATURE:
<223> OTHER INFORMATION: MITF conserved region 2 upstream primer

<400> SEQUENCE: 9
agtctgaagc aagagcactg g                                        21

<210> SEQ ID NO 10
<211> LENGTH: 21
<212> TYPE: DNA
<213> ORGANISM: Artificial Sequence
<220> FEATURE:
<223> OTHER INFORMATION: MITF conserved region 2 downstream primer

<400> SEQUENCE: 10
ctaacaagtg tgctccgtct c                                        21

<210> SEQ ID NO 11
<211> LENGTH: 21
<212> TYPE: DNA
<213> ORGANISM: Artificial Sequence
<220> FEATURE:
<223> OTHER INFORMATION: 5'U6 promoter primer

<400> SEQUENCE: 11
aaggtcgggc aggaagaggg c                                        21

<210> SEQ ID NO 12
<211> LENGTH: 24
<212> TYPE: DNA

```
<213> ORGANISM: Artificial Sequence
<220> FEATURE:
<223> OTHER INFORMATION: 3'H1 promoter primer

<400> SEQUENCE: 12
tatttgcatg tcgctatgtg ttct                                          24

<210> SEQ ID NO 13
<211> LENGTH: 19
<212> TYPE: DNA
<213> ORGANISM: Artificial Sequence
<220> FEATURE:
<223> OTHER INFORMATION: MITF gene forward primer

<400> SEQUENCE: 13
catcaccttc aacaacaac                                                19

<210> SEQ ID NO 14
<211> LENGTH: 18
<212> TYPE: DNA
<213> ORGANISM: Artificial Sequence
<220> FEATURE:
<223> OTHER INFORMATION: MITF gene reverse primer

<400> SEQUENCE: 14
atgctcatac tgctcctc                                                 18

<210> SEQ ID NO 15
<211> LENGTH: 19
<212> TYPE: DNA
<213> ORGANISM: Artificial Sequence
<220> FEATURE:
<223> OTHER INFORMATION: GAPDH gene forward primer

<400> SEQUENCE: 15
gaaggtgaag gtcggagtc                                                19

<210> SEQ ID NO 16
<211> LENGTH: 20
<212> TYPE: DNA
<213> ORGANISM: Artificial Sequence
<220> FEATURE:
<223> OTHER INFORMATION: GAPDH gene reverse primer

<400> SEQUENCE: 16
gaagatggtg atgggatttc                                               20

<210> SEQ ID NO 17
<211> LENGTH: 21
<212> TYPE: RNA
<213> ORGANISM: Artificial Sequence
<220> FEATURE:
<223> OTHER INFORMATION: negative control siRNA sense strand
<220> FEATURE:
<221> NAME/KEY: misc_feature
<222> LOCATION: (20)..(21)
<223> OTHER INFORMATION: n = deoxy-thymine

<400> SEQUENCE: 17
uucuccgaac gugucacgun n                                             21

<210> SEQ ID NO 18
<211> LENGTH: 21
<212> TYPE: RNA
<213> ORGANISM: Artificial Sequence
<220> FEATURE:
<223> OTHER INFORMATION: negative control siRNA antisense strand
```

```
<220> FEATURE:
<221> NAME/KEY: misc_feature
<222> LOCATION: (20)..(21)
<223> OTHER INFORMATION: n = deoxy-thymine

<400> SEQUENCE: 18
acgugacacg uucggagaan n                                             21
```

SIRNA MOLECULE FOR INHIBITING GROWTH OF MELANIN AND APPLICATION THEREOF

This application is a U.S. National Phase based on International Patent Application No. PCT/CN2012/082612, filed on Oct. 9, 2012, which claims priority to Chinese Patent Application No. 201110331472.1, filed on Oct. 27, 2011, both of which are incorporated herein by reference in their entirety.

FIELD OF THE INVENTION

The present invention relates to a siRNA molecule and application thereof and in particular to a siRNA molecule for inhibiting growth of melanin and application thereof.

BACKGROUND OF THE INVENTION

Microphthalmia-associated transcription factor (MITF) plays an important role in regulating development, differentiation and function of melanocytes. MITF has a basic-helix-loop-helix-leucine zipper (bHLHZip) structure (Hodgkinson C A et al, 1993, Cell, 744: 395-404). The MITF gene in humans is located on the third chromosome $3P^{14.1}$-$3P^{12.3}$ in humans. Studies have shown that it plays a critical role in regulating development, differentiation and function of pigment cells. Mutation of the MITF gene results in developmental deficit and functional impairment of pigment cells, as well as complex interactions between MITF and other signaling molecules.

MITF can regulate expression of a gene family for tyrosine, and thus participate in the regulation of melanogenesis. (Shibahara, S et al, Pigment Cell Res, 1998, 11: 329-336). The tyrosinase gene family has three members: tyrosinase, tyrosinase related protein-1 (TRP-1), and tyrosinase related protein-2 (TRP-2). Promoters of the genes all contain an "M box" structure with a "CATGTG" core, and MITF can bind to the structure to transactivate expression of the respective genes. By interaction with the promoters of the tyrosinase gene family, MITF, on the one hand, directs specific expression of the genes in melanocytes and, on the other hand, is involved in regulating melanogenesis in melanocytes by external stimuli. It has been found from the analysis of deletion and mutation in human tyrosine genes that, tyrosine promoters contain three structures: TDE, M box and E box. The three structures all contain a "CATGTG" core motif and are necessary for effective expression of tyrosine in pigment cells, and promoters with the same structures only leads to weak expression in non-pigment cells. Further studies have found that MITF can bind to these structures to stimulate transcriptional activity of the promoters. MITF itself is cell-specific and plays a critical role in specific expression of tyrosinase in melanocytes. TRP-1 and TRP-2 also have the M-box structure which is highly conserved among the tyrosine family, and MITF can bind to the M-box in the TRP-1 gene to activate its expression and direct its specific expression in melanocytes (Aksan I et al, Mol Cell Biol, 1998, 18(12): 6930-8).

Melanocytes are one of important constituents of skin cells, are of embryonic neural crest origin, have dendritic protrusions, and belong to gland cells. The synthesized melanin is secreted into keratinocytes via the dendritic protrusions, and is discharged from the body with shedding of keratinocytes and is present on the basal layer of the epidermis. Melanocytes give the skin its color through the synthesis of melanin, and also can absorb ultraviolet radiation to protect the body from being injured by ultraviolet radiation. Mammalian skin and hair colors are mainly determined by relative amount and distribution of melanin produced by melanocytes (Sturm R A et al, Bioessays, 1998, 20: 712). Melanin is further divided into Eu-melanin (brown/black) and Pheomelanin (red/yellow) (Newton J M et al, Mamma Genome, 2000, 11: 24). The regulation of development, differentiation and melanin synthesis of melanocytes is a complex process involving in many signaling molecules to create a complex signaling network in which MITF plays an important role.

RNA interference (RNAi) is a biological phenomenon which is ancient and highly conserved in evolution, which is a post-transcriptional gene silencing in which efficient specific degradation of homologous mRNA is induced by double-stranded RNA (dsRNA) (Andrew Fire et al, Nature, 1998, 391: 806-811). Small interfering RNAs (siRNAs) are effector molecules of RNAi, which are made up of two complementary RNA strands and have 21-23 nucleotides (nt) in length. Because the RNAi technology can specifically knock out or shut down expression of a particular gene, the technology has been widely used in various studies of functional genomics, infectious diseases and antiviral and antitumor therapies. Some studies have reported that by inhibiting the MITF gene by RNAi modulation, downstream tyrosinase (TYR) gene and tyrosinase related protein-1 (TRP-1) gene (Busca B et al, J Cell Biol, 2005, 49) can be regulated, thereby regulating the growth of melanin.

SUMMARY OF THE INVENTION

An object of the present invention is to provide a double-stranded siRNA molecule capable of efficiently targeting the MITF gene, screened by the siRNA molecular library technology, which is composed of a sense strand and an antisense strand below:

```
                                        (SEQ ID NO: 3)
    sense: 5'-GGGACACUGAGGAAAGGAGUGGANn-3'

(SEQ ID NO: 4)
    antisense: 5'-UCCACUCCUUUCCUCAGUGUCCCNn-3'
``` wherein N is cytidine C, guanosine G, adenosine A, uridine U; deoxycytidine dC, deoxyguanosine dG, deoxyadenosine dA, or deoxythymidine dT.

In other words, the backbone sequences of the double-stranded siRNA molecule are:

```
                                        (SEQ ID NO: 5)
    sense: 5'-GGGACACUGAGGAAAGGAGUGGA-3'

(SEQ ID NO: 6)
    antisense: 5'-UCCACUCCUUUCCUCAGUGUCCC-3'
```

In a preferred embodiment, the "Nn" at 3' end in the sequences above is the two deoxythymidine dTdT.

Another object of the present invention is to provide the applications of the above-described siRNA molecule for use in the preparation of freckle whitening cosmetics and medicines for treating diseases related to increased melanin.

The present invention involves screening a siRNA molecule library constructed for MITF genes involved in regulation of melanin formation using a high-flux screening method, in order to select siRNAs capable of effectively inhibiting melanin production, which inhibit the MITF gene by RNAi modulation, thereby regulating production of melanin.

The siRNAs targeting the MITF gene screened by the present invention can be used as an active ingredient in pharmaceutical preparations or cosmetics, for down regulating the expression of melanin genes in skin, to reduce pigment content and pigmentation, and remove skin spots such as senile plaque, pox imprint, pigmented spots, freckle, cyasma, or other pigment changes caused by the sun, inflammations, drugs and the like, thereby resulting in human skin whiting.

In vitro experiments have shown that, the antisense strand of the siRNA molecule of the present invention can specifically bind to the mRNA of the MITF gene and degrade the mRNA, in order to interfere with post-transcription translation process, down regulate expression of melanin-related genes, and eventually inhibit melanin production, without significant toxic side effects.

DETAILED DESCRIPTION

The siRNA molecule of the present invention is derived from a siRNA molecule library prepared for conserved regions of open reading frames of the MITF gene. The siRNA molecule technology used in the present invention is a patented technology of Biomics Biotech (China patent application No. 200710024217.6, titled "Preparation method for PCR high flux construction of siRNA whole site molecule library"), which has the advantages that, the prepared siRNA is randomly distributed in a segment of MITF open reading frames and has a controlled length in the range of 19-23 bp, and the hit rate of effective target sites is improved.

The siRNA can be prepared in many ways such as chemical synthesis, in vitro transcription, enzyme cleavage of long-chain dsRNA, vector expression of siRNA, PCR synthesis of siRNA expression elements. The presence of these methods provides a selection space for researchers and can be used to obtain better gene silencing efficiency.

As an alternative expression form of the siRNA molecule in cells, it can be prepared into a DNA expression cassette form such as U6 promotor-siRNA transcription template-H1 promotor.

The siRNA molecule of the present invention can be used as an active ingredient in freckle whitening cosmetics, and also used as an active ingredient in medicines for treating diseases associated with increased melanin.

For use, the siRNA molecule can be directly administered as a medicine onto a specific site (for example, pigment plaque) on a subject.

Preferably, the siRNA molecule is used as an active ingredient in freckle whitening cosmetics. For use, the siRNA molecule can be prepared with other auxiliary agents into any suitable formulation, as long as it is suitable for applications of the siRNA molecule and the activity of the siRNA molecule can be properly retained.

Optionally, any pharmaceutically acceptable auxiliary agent can be contained in the above-described pharmaceutical formulations, as long as it is suitable for an expected administration system and the activity of the siRNA molecule can be properly retained.

The following experimental scheme is designed to in order to achieve the design concept of the present invention and verify the effect of inhibiting melanin production by the selected siRNAs:

(1) Construction of a siRNA molecule library for open reading frames of an inhibitor of apoptosis MITF gene, the molecule library comprising siRNA effector molecules targeting the MITF gene, having a length ranging from 19-23 bp.

(2) Preparation of a siRNA expression cassette having a corresponding effect, having a structure of "U6 promotor-siRNA transcription template-H1 promotor", which facilitates in vitro screening.

(3) Use of real-time quantitative PCR, which determines inhibition of the MITF gene by the effector siRNA molecule transcribed from the siRNA expression cassette in cells.

(4) Chemical synthesis of siRNA screened from the above-described method, in which real-time quantitative PCR is further used in vitro cell experiments to determine mRNA expression level of the MITF gene.

(5) Determination of toxicity of the screened siRNA on cells using CCK8 method.

(6) Determination of the effect of the screened siRNA on melanin production in cells using reported method.

The following examples are intended only to illustrate the invention, not for limitation.

Example 1

Preparation of siRNA Molecule Library

Figure 1:
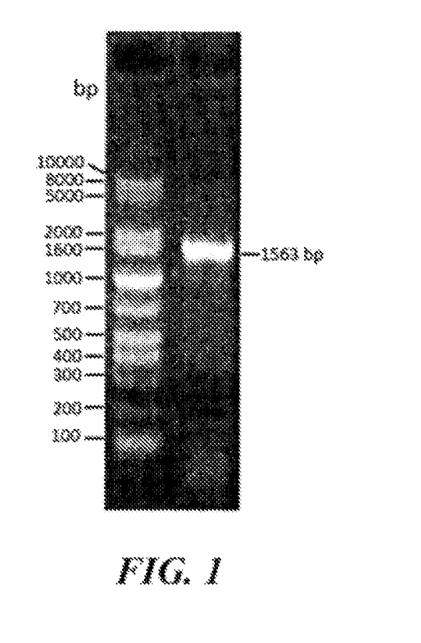
FIG. 1 is an agarose gel electrophoresis profile of open reading frames of conserved regions of the synthesized MITF gene, with the prepared DNA fragment having a size of 1563 bp. The left band represents a DNA molecular weight Marker (strandard reference).

1. Obtaining MITF gene target sequence: there are eight transcript variant sequences in total for MITF gene in US NCBI database, and one representative transcript variant 1 (NCBI database number: NM_198159) Open Reading Frame (ORF) was synthesized by Biomics Biotech using full gene synthesis, giving the ORF sequence of MITF having a length of 1563 bp (the agarose gel electrophoresis profile of the full length gene is shown in FIG. 1).

Two segments of conserved regions of MITF gene were prepared using PCR method, respectively using the following primers:

```
conserved region 1 upstream primer:
                                    (SEQ ID NO: 7)
5'-AGGTGCAGACCCACCTCGAAA-3';

conserved region 1 downstream primer:
                                    (SEQ ID NO: 8)
5'-TGTGAGCTCCCTTTTTATGTTG-3';

conserved region 2 upstream primer:
                                    (SEQ ID NO: 9)
5'-AGTCTGAAGCAAGAGCACTGG-3';

conserved region 2 downstream primer:
                                    (SEQ ID NO: 10)
5'-CTAACAAGTGTGCTCCGTCTC-3',
```

The conserved regions were amplified as target sequence for constructing siRNA molecule library, with an amplified length of 527 bp (SEQ ID NO: 1) and 683 bp (SEQ ID NO: 2), respectively.

```
conserved region 1: 527bp
                                    (SEQ ID NO: 1)
 481                aggtg cagacccacc tcgaaaaccc 541 caccaagtac cacatacagc aagcccaacg gcagcaggta
     aagcagtacc tttctaccac 601 tttagcaaat aaacatgcca accaagtcct gagcttgcca
     tgtccaaacc agcctggcga 661 tcatgtcatg ccaccggtgc cggggagcag cgcacccaac
     agcccatgg ctatgcttac 721 gcttaactcc aactgtgaaa aagagggatt ttataagttt
     gaagagcaaa acagggcaga 781 gagcgagtgc ccaggcatga acacacattc acgagcgtcc
     tgtatgcaga tggatgatgt 841 aatcgatgac atcattagcc tagaatcaag ttatggtgag
     gaaatcttgg gcttgatgga 901 tcctgctttg caaatggcaa atacgttgcc tgtctcggga
     aacttgattg atctttatgg 961 aaaccaaggt ctgcccccac caggcctcac catcagcaac
     tcctgtccag ccaaccttcc 1021 caacataaaa agggagctca ca conserved region 2: 683bp
                                    (SEQ ID NO: 2)
1021       agtctga agcaagagca ctggccaaag agaggcagaa 1081 aaaggacaat cacaacctga ttgaacgaag aagaagattt
     aacataaatg accgcattaa 1141 agaactaggt actttgattc ccaagtcaaa tgatccagac
     atgcgctgga acaagggaac 1201 catcttaaaa gcatccgtgg actatatccg aaagttgcaa
     cgagaacagc aacgcgcaaa 1261 agaacttgaa aaccgacaga agaaactgga gcacgccaac
     cggcatttgt tgctcagaat
```

```
1321 acaggaactt gaaatgcagg ctcgagctca tggactttcc
     cttattccat ccacgggtct 1381 ctgctctcca gatttggtga atcggatcat caagcaagaa
     cccgttcttg agaactgcag 1441 ccaagacctc cttcagcatc atgcagacct aacctgtaca
     acaactctcg atctcacgga 1501 tggcaccatc accttcaaca caacctcgg aactgggact
     gaggccaacc aagcctatag 1561 tgtccccaca aaaatgggat ccaaactgga agacatcctg
     atggacgaca ccctttctcc 1621 cgtcggtgtc actgatccac tcctttcctc agtgtcccc
     ggagcttcca aaacaagcag 1681 ccggaggagc agtatgagca tggaagagac ggagcacact
     tgttag
```

Figure 2:
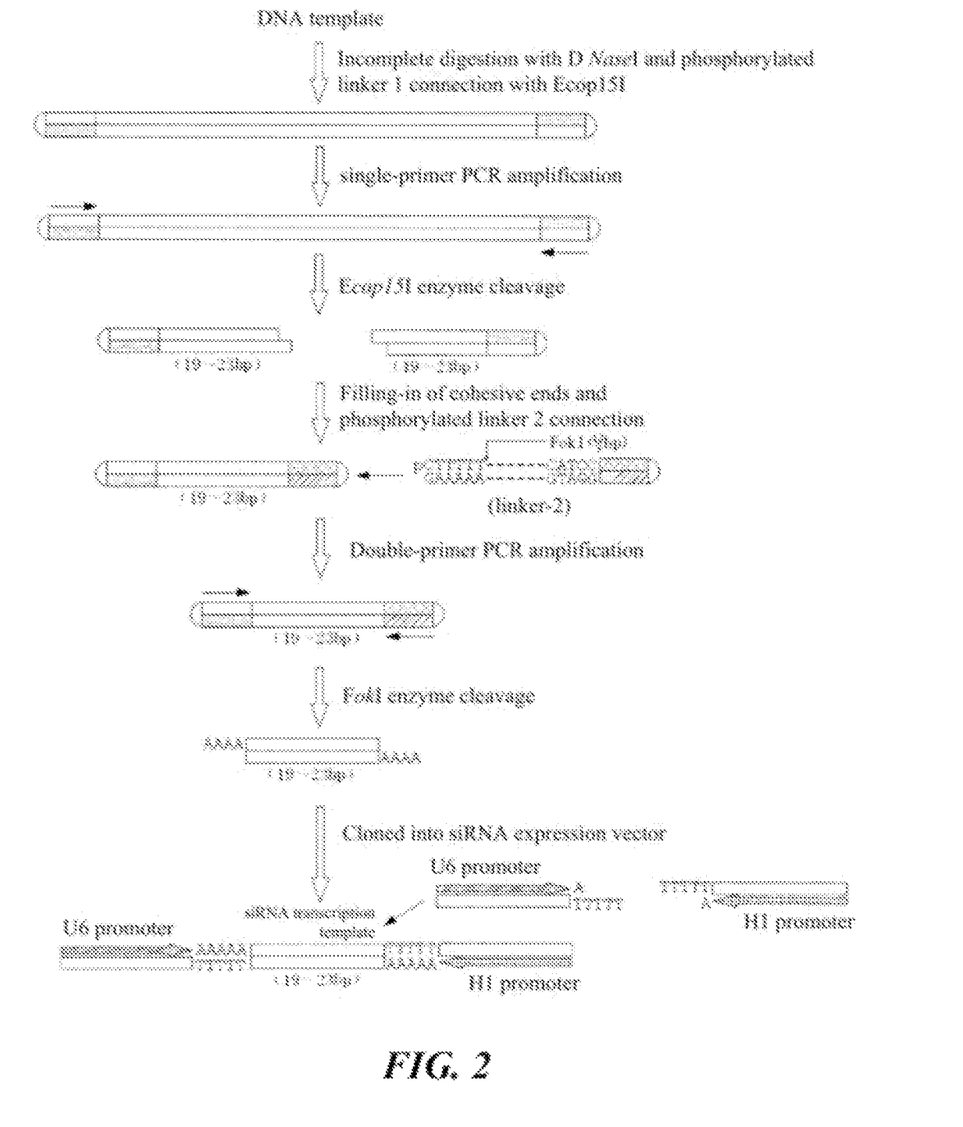
FIG. 2 is a schematic flow of construction of a siRNA molecue library.

2. Constructing siRNA molecule library: the patented technology of Biomics Biotech was used to construct siRNA molecule library (patent application No.: 200710024217.6, titled "Preparation method for PCR high flux construction of siRNA whole site molecule library"), with a construction schematic flow shown in FIG. 2.

The siRNA molecule library for conserved regions of MITF was successfully constructed, and clones were randomly chosen for sequencing, with a controlled length ranging from 19-23 bp, showing site diversity and length diversity.

Example 2

Preparation of siRNA Expression Cassette and Target Screening

1. Major Instruments, Reagents and Materials 1.1 Instruments: PCR apparatus (ABI); real-time quantitative PCR apparatus (Bio-Rad); agarose gel electrophoresis system (Beijing Liuyi instrument factory); cell incubator (Thermo) etc.

1.2 Reagents and materials: 1 kb plus DNA Ladder (Invitrogen); Pfu DNA polymerase (Biomics Biotech); Agarose (BBI); dNTP (Sangon Biotech (Shanghai)); Agarose gel purification kit (Biomics Biotech), Lipofectamin™ 2000 (Invitrogen), DMEM medium (Gibco), TurboCapture mRNA kit (QIAGEN), EzOmics™ One-Step qPCR kit (Biomics Biotech) etc. Other biochemical reagents were purchased from Sangon Biotech (Shanghai), and formulated into working solutions by Biomics Biotech.

1.3 PCR primers (synthesized by Biomics Biotech) having the following sequences:

```
5'U6 promoter primer:
                                    (SEQ ID NO: 11)
5'-AAGGTCGGGCAGGAAGAGGGC-3';

3'H1 promoter primer:
                                    (SEQ ID NO: 12)
5'-TATTTGCATGTCGCTATGTGTTCT-3';

MITF gene forward primer:
                                    (SEQ ID NO: 13)
5'-CATCACCTTCAACAACAAC-3';

MITF gene reverse primer:
                                    (SEQ ID NO: 14)
5'-ATGCTCATACTGCTCCTC-3';
```

-continued

```
GAPDH gene forward primer:
                                (SEQ ID NO: 15)
5'-GAAGGTGAAGGTCGGAGTC-3';

GAPDH gene reverse primer:
                                (SEQ ID NO: 16)
5'-GAAGATGGTGATGGGATTTC-3'.
```

Figure 3:
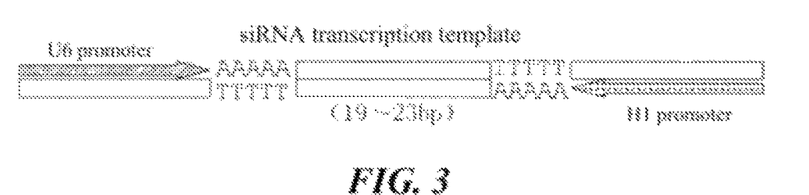
FIG. 3 is a schematic representation of the structure of a "U6-siRNA transcription template-H1" expression cassette.

2. Preparation of siRNA Expression Cassette 2.1 PCR amplification to prepare siRNA expression cassette "U6-siRNA transcription template-H1": with MITF siRNA positive clone plasmid as template, the PCR amplification was performed using high-fidelity enzyme Pfu DNA polymerase (the schematic diagram of the expression cassette is shown in FIG. 3).

Figure 4:
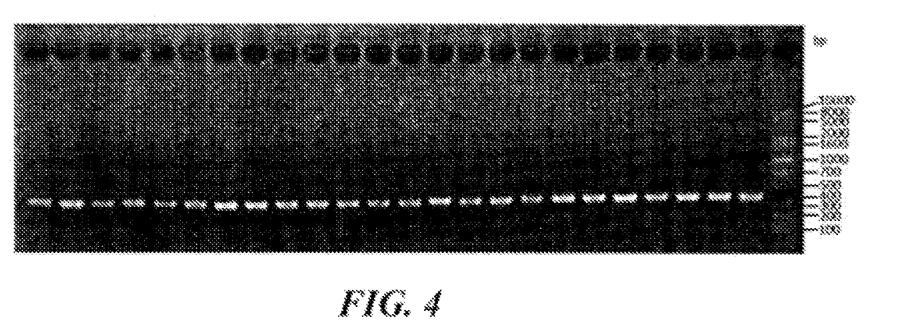
FIG. 4 is an agarose gel electrophoresis profile (partial) of the PCR prepared "U6-siRNA transcription template-H1" expression cassette after purification. In the figure, the rightmost band represents a DNA molecular weight Marker (strandard reference).

Each PCR reaction system was (50 μl reaction system): 0.5 μl template DNA (10-50 ng), 1 μl 5'U6 promoter primer (10 μM), 1 μl 3'H1 promoter primer (10 μM), 1 μl dNTP (10 mM), 0.5 μl Pfu DNA polymerase, q.s. ddH$_2$O to 50 μl, and the reation conditions were: 95° C. predenature for 1 min, 95° C. denature for 15 sec, 58° C. anneal for 30 sec, 72° C. extension for 30 sec, 20 cycles. The expression cassette obtained by PCR amplification was separated with 1.0% agarose gel electrophoresis, and purified with the agarose gel purification kit. From 1.0% agarose gel electrophoresis, the PCR product has a single band with a fragment size of about 380-384 bp, which meets the design requirements (the agarose gel electrophoresis profile is shown in FIG. 4).

3. Target Screening 3.1 Cell culture: the melanoma cell A375 was cultured in the DMEM medium containing 10% FBS in a 37° C., 5% CO$_2$ incubator.

3.2 Cell plating and transfection: the cell was seeded in a 96 well plate at 1×10$^5$/well, was cultured overnight in an antibody-free DMEM medium containing 10% FBS in a 37° C., 5% CO$_2$ incubator. Transfection was performed following the instructions with Lipofectamin™ 2000, and the DNA amount in the "U6-siRNA transcription template-H1" expression cassette was added at 0.2 μg/well.

3.3 Real-time quantitative PCR to determine mRNA level of MITF gene: the cell RNA was extracted and purified with the mRNA extraction and purification kit TurboCapture mRNA kit, following the instructions of the kit, and RNA was dissolved in 80 μl RNase-free water/well, and 4 μl RNA was taken as template for real-time quantitative PCR reaction.

The mRNA expression level of MITF gene in samples was determined with gene-specific primers, and also the housekeeping gene GAPDH was amplified as internal reference. Each reaction was performed in triplicates. 25 μl reaction system was established below: 4 μl template RNA, 12.5 μl 2× Master Mix, 1 μl forward primer (6 μM), 1 μl reverse primer (6 μM), 0.5 μl 50×SYBR Green I, q.s. RNase-free water to 25 μl. The reaction conditions were: 40° C. reverse transcription for 30 min, 95° C. predenature for 7 min, 95° C. denature for 20 sec, 60° C. anneal for 30 sec, 72° C. extension for 30 sec, 45 cycles, and the solubility curve was determined.

Figure 5:
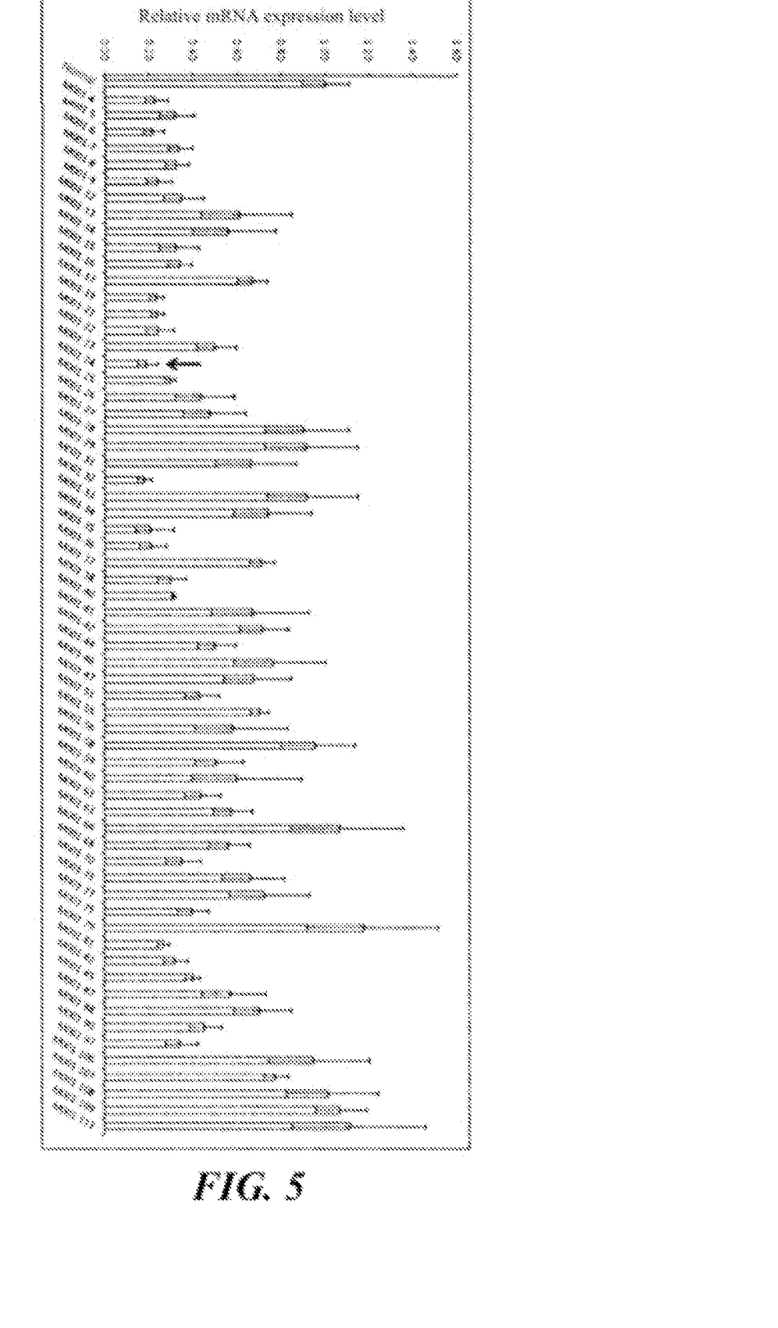
FIG. 5 is a column chart of mRNA expression level from real-time PCR assay of MITF gene after cell transfection with the "U6-siRNA transcription template-H1" expression cassette. The horizontal axis represents various treatment groups and the vertical axis represents mRNA expression of MITF relative to GAPDH, in which the arrow refers to M001-24 transfection group, and the "normal" refers to non-transfected normal culture cell group.

3.4 Results analysis: the experimental results were analyzed by $2^{-\Delta\Delta ct}$ method, and a column plot was drawn as shown in FIG. 5. The results show that siRNA at multiple sites of MITF present good silencing effect, and in particular, M001-24 reaches 81%, compared to non-transfected group.

It is particularly noted that, M001-24 sense strand sequence corresponds to positions 1636-1658 (underlined tccactcctttcctcagtgtccc) in MITF gene conserved regions.

Example 3

Silencing Effect Verification with Chemically Synthesized siRNA

1. Major Instruments, Reagents and Materials 1.1 Instruments: nucleic acid synthesizer (GE), PCR apparatus (ABI); real-time quantitative PCRapparatus (Bio-Rad); cell incubator (Thermo) etc.

1.2 Reagents and materials: Lipofectamin™ 2000 (Invitrogen), DMEM medium (Gibco), TurboCapture mRNA kit (QIAGEN), EzOmics™ One-Step qPCR kit (Biomics Biotech) etc. Other biochemical reagents were purchased from Sangon Biotech (Shanghai), and formulated into working solutions by Biomics Biotech.

1.3 Real-time quantitative PCR primers (synthesized by Biomics Biotech) having the following sequences:

```
MITF gene forward primer:
                                (SEQ ID NO: 13)
5'CATCACCTTCAACAACAAC-3';

MITF gene reverse primer:
                                (SEQ ID NO: 14)
5'ATGCTCATACTGCTCCTC-3';

GAPDH gene forward primer:
                                (SEQ ID NO: 15)
5'-GAAGGTGAAGGTCGGAGTC-3';

GAPDH gene reverse primer:
                                (SEQ ID NO: 16)
5'-GAAGATGGTGATGGGATTTC-3'.
```

2. Preparation of siRNA via Chemical Synthesis

RNAs of sense strand and antisense strand of M001-24 were synthesized using a nucleic acid synthesizer (AKTA Oligo Pilot) owned by Biomics Biotech, respectively. Purification was performed, and the sense strand and the corresponding antisense strand were annealed into a siRNA duplex, aliquoted in 1OD/tube, finally freeze-dried, and dissolved to 20 μM with RNase-free water befer transfection.

The siRNA sequence (5'-3') of the negative control group was:

```
                                (SEQ ID NO: 17)
sense: UUCUCCGAACGUGUCACGUdTdT, (SEQ ID NO: 18)
antisense: ACGUGACACGUUCGGAGAAdTdT.
```

3. Silencing Efficiency Verification 3.1 Cell culture: the melanoma cell A375 was cultured in the DMEM medium containing 10% FBS in a 37° C., 5% CO$_2$ incubator.

3.2 Cell plating and transfection: the cell was seeded in a 96 well plate at 1×10$^5$/well, and was cultured overnight in an antibody-free DMEM medium containing 10% FBS in a 37° C., 5% CO$_2$ incubator.

Transfection was performed following the instructions with Lipofectamin™ 2000, and the RNA was added at 10 nM/well.

3.3 Real-time quantitative PCR to determine mRNA level of MITF gene: the cell RNA was extracted and purified with the mRNA extraction and purification kit TurboCapture mRNA kit, following the instructions of the kit, and dissolved in 80 μl RNase-free water/well, and 4 μl RNA was taken as template for real-time quantitative PCR reaction.

The mRNA expression level of MITF in samples was determined with gene-specific primers, and also the housekeeping gene GAPDH was amplified as internal reference. Each reaction was performed in triplicates. 25 µl reaction system was established below: 4 µl template RNA, 12.5 µl 2× Master Mix, 1 µl forward primer (6 µM), 1 µl reverse primer (6 µM), 0.5 µl 50×SYBR Green I, q.s. RNase-free water to 25 µl. The reaction conditions were: 40° C. reverse transcription for 30 min, 95° C. predenature for 7 min, 95° C. denature for 20 sec, 60° C. anneal for 30 sec, 72° C. extension for 30 sec, 45 cycles.

Figure 6:
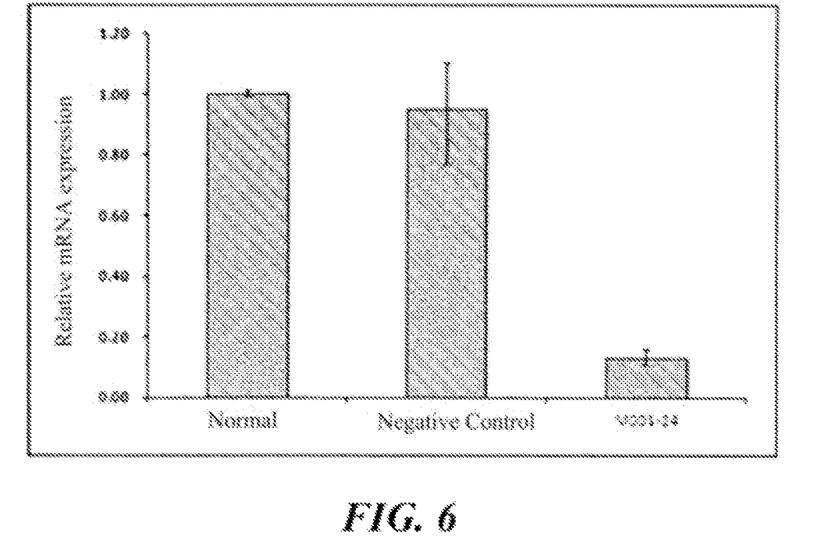
FIG. 6 is a column chart of mRNA expression level from real-time PCR assay of MITF gene after cell transfection with the chemically synthesized siRNA. The horizontal axis represents various treatment groups and the vertical axis represents mRNA expression of MITF relative to GAPDH, in which M001-24 refers to M001-24 transfection group, "normal" refers to non-transfected normal culture cell group, and "negative control" is negative control siRNA transfection group.

3.4 Results analysis: the experimental results were analyzed by $2^{-\Delta\Delta ct}$ method, and a column plot was drawn as shown in FIG. 6. The results show that M001-24 targeting MITF gene reaches silencing effect of 87%.

Example 4

Cell Toxicity Assay

Figure 7:
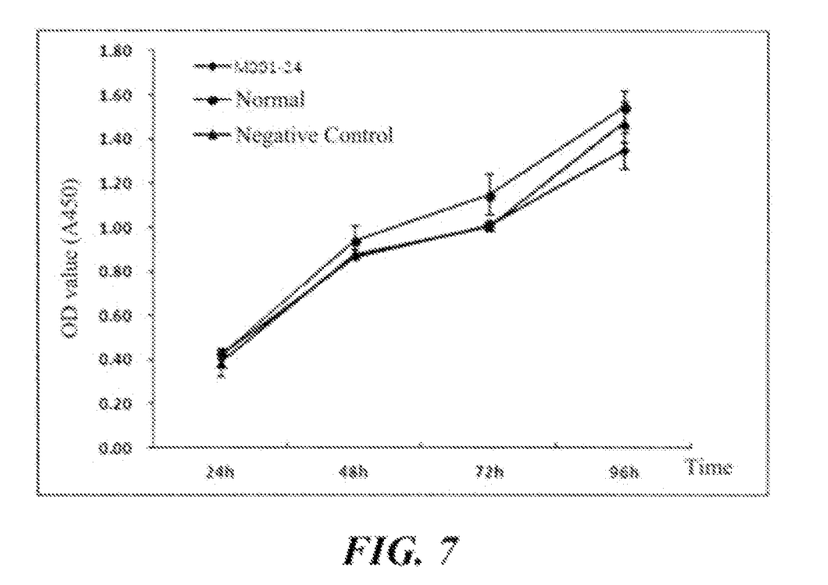
FIG. 7 is a cell growth curve after cell transfection with siRNA. The horizontal axis represents various treatment groups and the vertical axis represents OD valve ($A_{450}$ valve) measured from various treatment groups, in which M001-24 refers to M001-24 transfection group, "normal" refers to non-transfected normal culture cell group, and "negative control" is negative control siRNA transfection group.

1. Major Instruments, Reagents and Materials
1.1 Instruments: cell incubator (Thermo); microplate reader (Bio-Rad) etc.
1.2 Reagents and materials: Lipofectamin™ 2000 (Invitrogen), DMEM medium (Gibco), CCK8 kit (DOJINDO) etc. Other biochemical reagents were purchased from Sangon Biotech (Shanghai), and formulated into working solutions by Biomics Biotech.
2. Cell Toxicity Assay
2.1 Cell culture: the melanoma cell A375 was cultured in the DMEM medium containing 10% FBS in a 37° C., 5% CO2 incubator.
2.2 Cell plating and transfection: the cell was seeded in a 96 well plate at $1\times10^5$/well, was cultured overnight in an antibody-free DMEM medium containing 10% FBS in a 37° C., 5% $CO_2$ incubator. Transfection was performed following the procedures with Lipofectamin™ 2000 (Invitrogen), and the tested various RNA molecules were added at 10 nM/well.
2.3 CCK-8 assay: the determination was performed at various time points. A volume of 1/10 medium of CCK-8 solution was added in each well in plate. It was further incubated for 0.5-4 h in a cell incubator. The absorbance at 450 nm was determined with the miroplate reader.
2.4 Results analysis: according to measured $A_{450}$ values (OD values), a growth curve was plotted as shown in FIG. 7. Compared to normal group, M001-24 has a certain growth inhibition effect on melanoma cell, without significant toxic effects.

Example 5

Melanin Content Determination

Figure 8:
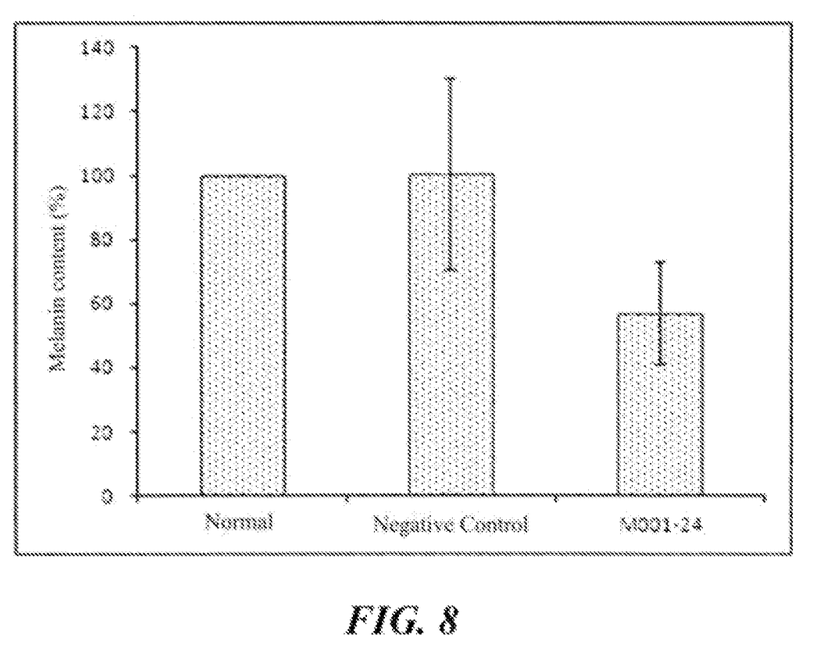
FIG. 8 is a column chart of melanin content in cells after cell transfection with siRNA compared to normal group. The horizontal axis represents various treatment groups and the vertical axis represents melanin content by percent relative to normal group, in which M001-24 refers to M001-24 transfection group, "normal" refers to non-transfected normal culture cell group, and "negative control" is negative control siRNA transfection group.

1. Major Instruments, Reagents and Materials
1.1 Instruments: cell incubator (Thermo); microplate reader (Bio-Rad) etc.
1.2 Reagents and materials: Lipofectamin™ 2000 (Invitrogen), DMEM medium (Gibco), trypsin (Gibco), CCK8 kit (DOJINDO) etc. Other biochemical reagents were purchased from Sangon Biotech (Shanghai), and formulated into working solutions by Biomics Biotech.
2. Cell Toxicity Assay
2.1 Cell culture: the melanoma cell A375 was cultured in the DMEM medium containing 10% FBS in a 37° C., 5% CO2 incubator.
2.2 Cell plating and transfection: the cell was seeded in a 96 well plate at $1\times10^5$/well, was cultured overnight in an antibody-free DMEM medium containing 10% FBS in a 37° C., 5% $CO_2$ incubator. Transfection was performed following the procedures with Lipofectamin™ 2000 (Invitrogen), and the tested various RNA molecules were added at 10 nM/well.
2.3 Melanin content determination: the method of Jones K et al (Jones K et al. *Pigment Cell Res* 2002; 15:335-40) was modified for melanin content determination. A375 cell was transfected for 72 h, and then washed with PBS twice and digested with 0.25% trypsin. The complete medium was added to terminate digestion. The cell was centrifuged at 1,000 rpm for 5 min, and the supernatant was discarded. The cell was resuspended by adding 1 ml PBS per well, counted with a hemocytometer, and then centrifuged at 1,000 rpm for 5 min, and the supernatant was discarded. The cell pellets were dried in a superclean bench, and cells were dissolved per $10^6$ cells in 500 µl N NaOH solution containing 1% DMSO. It was heated at 80° C. for 1 h and then cooled. The absorbance at 475 nm was determined with the miroplate reader.
2.4 Results analysis: according to measured $A_{475}$ values (OD values), a column chart was plotted as shown in FIG. 8. Compared to normal group, in M001-24 treatment group, melanin content was decreased by 43%, indicating that melanin production was significantly inhibited.

The invention claimed is:

1. A double-stranded siRNA molecule, having the following sequences:

sense: 5'GGGACACUGAGGAAAGGAGUGGANn-3' (SEQ ID NO: 3)

antisense: 5'-UCCACUCCUUUCCUCAGUGUCCCNn-3'. (SEQ ID NO: 4)

wherein N is deoxythymidine dT; and n is 0 or 2.

2. An application of the siRNA molecule of claim 1 for use in freckle whitening cosmetics.

3. An application of the siRNA molecule of claim 1 for use in the preparation of medicines for treating diseases related to increased melanin.

* * * * *